(12) United States Patent
Tanaka et al.

(10) Patent No.: US 8,658,779 B2
(45) Date of Patent: *Feb. 25, 2014

(54) PERILLA-DERIVED PROMOTER FUNCTIONING IN PETALS

(75) Inventors: Yoshikazu Tanaka, Mishima-gun (JP); Masako Mizutani, Mishima-gun (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 126 days.

This patent is subject to a terminal disclaimer.

(21) Appl. No.: 13/265,752

(22) PCT Filed: Mar. 9, 2010

(86) PCT No.: PCT/JP2010/053886
§ 371 (c)(1),
(2), (4) Date: Oct. 21, 2011

(87) PCT Pub. No.: WO2010/122848
PCT Pub. Date: Oct. 28, 2010

(65) Prior Publication Data
US 2012/0042421 A1    Feb. 16, 2012

(30) Foreign Application Priority Data

Apr. 24, 2009   (JP) ................. 2009-107057

(51) Int. Cl.
*C07H 21/04* (2006.01)
*C12N 15/09* (2006.01)
*C12N 15/63* (2006.01)
*C12N 15/82* (2006.01)
*A01H 3/00* (2006.01)
*A01H 5/00* (2006.01)

(52) U.S. Cl.
USPC .......... 536/24.1; 800/295; 800/298; 800/323; 800/287; 536/22.1; 435/320.1

(58) Field of Classification Search
None
See application file for complete search history.

(56) References Cited

U.S. PATENT DOCUMENTS

| 7,105,719 B1 | 9/2006 | Ashikari et al. |
| 2011/0126320 A1 | 5/2011 | Tanaka et al. |
| 2012/0073017 A1* | 3/2012 | Noda et al. ............. 800/282 |

FOREIGN PATENT DOCUMENTS

| EP | 1652916 A1 | 5/2006 |
| JP | 2003-235583 | 8/2003 |
| WO | WO-94/28140 A1 | 12/1994 |
| WO | WO-2005/017147 A1 | 12/1994 |
| WO | WO-96/25500 A1 | 8/1996 |
| WO | WO-01/72984 A1 | 10/2001 |
| WO | 2005/017147 | 2/2005 |

OTHER PUBLICATIONS

Anderson. Anthocyanins. Encyclopedia of Life Sciences. 2002. pp. 1-8.*
Kim et al. A 20 nucleotide upstream element is essential for the nopaline synthase (nos) promoter activity. Plant Molecular Biology. 1994. 24: 105-117.*
Kennell. Principles and practices of nucleic acid hybridization. Progress in Nucleic Acid Research and Molecular Biology. 1971. 11: 259-301.*
Maniatis et al. Molecular Cloning. Cold Spring Harbor Laboratory. 1982. 324-389.*
Bovy et al. Genetic modification of the vase-life of carnation. ACTA Horticulture. 1995. 405: 179-189.*
International Search Report dated Jun. 1, 2010 for International Application No. PCT/JP2010/053886 filed Mar. 9, 2010.
K. Yonekura-Sakakibara et al., "Molecular and Biochemical Characterization of a Novel Hydroxycinnamoyl-CoA: Anthocyanin 3-*O*-Glucoside-6"-*O*-Achyltransferase from *Perilla frutescens*", Plant Cell Physiol., 2000, vol. 41, p. 495-502.
Y. Tanaka et al., "Biosynthesis of plant pigments: anthocryanins, betalains and carotenoids", The Plant Journal, 2008, vol. 54, p. 733-749.
R. Koes et al., "Flavonoids: a colorful model for the regulation and evolution of biochemical pathways", Trends in Plant Science, May 2005, vol. 10, No. 5, p. 236-242.
P. Elomaa et al., "Activation of Anthocyanin Biosynthesis in *Gerbera hybrida* (Asteraceae) Suggests Conserved Protein-Protein and Protein-Promoter Interactions between the Anciently Diverged Monocots and Eudicots", Plant Physiology, Dec. 2003, vol. 133, pp. 1831-1842.
Tanaka et al., "Biosynthesis of plant pigments: anthocyanins, betalains and carotenoids," Plant Journal, (2008), vol. 54, pp. 733-749.
Kondo et al., "Structure of Malonylshisonin, a Genuine Pigment in Purple Leaves of *Perilla ocimoides* L. var. *crispa* Benth," Agric. Biol. Chem., vol. 53, No. 3, pp. 797-800 (1989).
Mitsuhara et al., "Efficient Promoter Cassettes for Enhanced Expression of Foreign Genes in Dicotyledonous and Monocotyledonous Plants," Plant Cell Physiol., vol. 37, No. 1, pp. 49-59 (1996).
Comai et al., "Novel and useful properties of a chimeric plant promoter combining CaMV 35S and MAS elements," Plant Molecular Biology, vol. 15, pp. 373-381, (1990).
Stam et al., "The Silence of Genes in Transgenic Plants," Annals of Botany, vol. 79, pp. 3-12, (1997).
European Search Report dated Nov. 7, 2012 issued in PCT Application No. PCT/JP2010053886.
Chandler S. et al., "Genetic modification in floriculture", Critical Review in Plant Sciences, CRC Press, Boca Raton, FL, US,, vol. 26, No. 4, Jul. 1, 2007, pp. 169-197, XP002587683, ISSN: 0735-2689, DOI: 10.1080/07352680701429381, pp. 174-181.

* cited by examiner

*Primary Examiner* — Cathy Kingdon Worley
*Assistant Examiner* — Ashley K Buran
(74) *Attorney, Agent, or Firm* — Drinker Biddle & Reath LLP (57) ABSTRACT

A transcriptional regulatory region of perilla anthocyanin 3-acyltransferase is useful for altering the flower color of plants.

5 Claims, 2 Drawing Sheets

SEQUENCE LISTING

```
<160> NUMBER OF SEQ ID NOS: 8

<210> SEQ ID NO 1
<211> LENGTH: 1096
<212> TYPE: DNA
<213> ORGANISM: Perilla frutescens
<220> FEATURE:
<221> NAME/KEY: promoter
<222> LOCATION: (1)..(1096)
<223> OTHER INFORMATION: anthocyanin 3-acyl transferase promoter

<400> SEQUENCE: 1
aactattatg atcccacaga gttttttgaca gatgagtctt caggaggaga tgctgaacct     60
tttcactact ctactgaacg catcacaagt ttatcggctt atatgactaa tagggatcaa    120
cttcacaaca gagaggctca tagagctctt aaagaggatt tgatcgagca catatggaaa    180
aaattcggca ctaactaaat atataattta cgttttatgc actcgtaatt taaaatttca    240
tgtgtctcat tgtagtttat ttaattatgt tttcactctt gtaattttta ttttgttgtg    300
aagtaaatta tgaatttata attatatggg taattttttg ataattatgc aattaaaaat    360
aattaatatt ttttaaatgc aagagaaaaa tgttatttta ataacatgtt cttattaaaa    420
aataaaatga taaatatttt atgtaggttg ggagaaaatg aaaaaataat attttatttg    480
```

```
aaggttgggt tggatgaggt cactgatggg agtataaata atactccctc cgtcccataa      540
ttattgtcca ttattccttt tgggatgtc ccaaaattat agtcctattc taaattggga       600
ttgtatttaa atattctttt acaaatataa ccctatttga tatagtatga atgcaattaa      660
tatagtaaaa aaataagggc aatataggat aattattgta aattgtatat ttccaataca      720
tattaaatgt gatttcttaa tctgtgtgaa ataggaagt ggactataat tatgggacgg       780
agggagtata aagttggagg ttgtggatgt ggaggagaaa gaaattaata ttttatttaa      840
agattggatt aaaggaggtc actgatgtgg gtagtcttag aggaaatgta gtcttagagg      900
aaatctgccc agcaaaataa aataataagt aaataaataa actaaatatg tattgaatgc      960
gacatctagc aatatagcca catatatagt gcagtagcac gcagcgctcg ttactcgtca     1020
gtcgtcaaag aatggtaagt atagaaaagc atctttaaat aacacaccaa aaaccacagc     1080
tacgttcaac accgcc                                                    1096
```

<210> SEQ ID NO 2
<211> LENGTH: 4087
<212> TYPE: DNA
<213> ORGANISM: Perilla frutescens
<220> FEATURE:
<221> NAME/KEY: CDS
<222> LOCATION: (1097)..(2443)
<223> OTHER INFORMATION: pSPB3311, anthocyanin 3-acyl transferase
      promoter + CDS + terminator

<400> SEQUENCE: 2

```
aactattatg atcccacaga gttttttgaca gatgagtctt caggaggaga tgctgaacct       60
tttcactact ctactgaacg catcacaagt ttatcggctt atatgactaa tagggatcaa      120
cttcacaaca gagaggctca tagagctctt aaagaggatt tgatcgagca catatggaaa      180
aaattcggca ctaactaaat atataattta cgttttatgc actcgtaatt taaaatttca      240
tgtgtctcat tgtagtttat ttaattatgt tttcactctt gtaatttta ttttgttgtg        300 aagtaaatta tgaatttata attatatggg taattttttg ataattatgc aattaaaaat      360
aattaatatt ttttaaatgc aagagaaaaa tgttatttta ataacatgtt cttattaaaa      420
aataaaatga taaatatttt atgtaggttg ggagaaaatg aaaaaataat attttatttg      480
aaggttgggt tggatgaggt cactgatggg agtataaata atactccctc cgtcccataa      540
ttattgtcca ttattccttt tgggatgtc ccaaaattat agtcctattc taaattggga       600
ttgtatttaa atattctttt acaaatataa ccctatttga tatagtatga atgcaattaa      660
tatagtaaaa aaataagggc aatataggat aattattgta aattgtatat ttccaataca      720
tattaaatgt gatttcttaa tctgtgtgaa ataggaagt ggactataat tatgggacgg       780
agggagtata aagttggagg ttgtggatgt ggaggagaaa gaaattaata ttttatttaa      840
agattggatt aaaggaggtc actgatgtgg gtagtcttag aggaaatgta gtcttagagg      900
aaatctgccc agcaaaataa aataataagt aaataaataa actaaatatg tattgaatgc      960
gacatctagc aatatagcca catatatagt gcagtagcac gcagcgctcg ttactcgtca     1020
gtcgtcaaag aatggtaagt atagaaaagc atctttaaat aacacaccaa aaaccacagc     1080
tacgttcaac accgcc atg acc acc acc gtg atc gaa acg tgt aga gtt ggg     1132
                  Met Thr Thr Thr Val Ile Glu Thr Cys Arg Val Gly
                    1               5                  10 cca ccg ccg gac tcg gtg gcg gag caa tcg ttg ccg ctc aca ttc ttc       1180
Pro Pro Pro Asp Ser Val Ala Glu Gln Ser Leu Pro Leu Thr Phe Phe
          15                  20                  25
```

```
gac atg acg tgg ctg cat ttt cat ccc atg ctt cag ctc ctc ttc tac    1228
Asp Met Thr Trp Leu His Phe His Pro Met Leu Gln Leu Leu Phe Tyr
    30              35              40 gaa ttc cct tgt tcc aag caa cat ttc tca gaa tcc atc att cca aaa    1276
Glu Phe Pro Cys Ser Lys Gln His Phe Ser Glu Ser Ile Ile Pro Lys
45              50              55              60 ctc aaa caa tct ctc tct aaa act ctc ata cac ttc ttc cct ctc tca    1324
Leu Lys Gln Ser Leu Ser Lys Thr Leu Ile His Phe Phe Pro Leu Ser
                65              70              75 tgc aat tta atc tac cct tca tct ccg gag aaa atg ccc gag ttt cgg    1372
Cys Asn Leu Ile Tyr Pro Ser Ser Pro Glu Lys Met Pro Glu Phe Arg
            80              85              90 tat cta tcg ggg gac tcg gtt tct ttc act atc gca gaa tct agc gac    1420
Tyr Leu Ser Gly Asp Ser Val Ser Phe Thr Ile Ala Glu Ser Ser Asp
        95              100             105 gac ttc gat gat ctc gtc gga aat cgc gca gaa tct ccc gtt agg ctc    1468
Asp Phe Asp Asp Leu Val Gly Asn Arg Ala Glu Ser Pro Val Arg Leu
    110             115             120 tac aac ttc gtc cct aaa ttg ccg cag att gtc gaa gaa tct gat aga    1516
Tyr Asn Phe Val Pro Lys Leu Pro Gln Ile Val Glu Glu Ser Asp Arg
125             130             135             140 aaa ctc ttc caa gtt ttc gcc gtg cag gtg act ctt ttc cca ggt cga    1564
Lys Leu Phe Gln Val Phe Ala Val Gln Val Thr Leu Phe Pro Gly Arg
                145             150             155 ggc gtc ggt att gga ata gca acg cat cac acc gtt agc gat gcc ccg    1612
Gly Val Gly Ile Gly Ile Ala Thr His His Thr Val Ser Asp Ala Pro
            160             165             170 tcg ttt ctc gcc ttt ata acg gct tgg gct tgg atg agc aaa cac att    1660
Ser Phe Leu Ala Phe Ile Thr Ala Trp Ala Trp Met Ser Lys His Ile
        175             180             185 gaa gat gaa gat gaa gag ttt aaa tct ttg cca gtt ttc gat aga tcc    1708
Glu Asp Glu Asp Glu Glu Phe Lys Ser Leu Pro Val Phe Asp Arg Ser
    190             195             200 gtc ata aaa tat ccg acg aaa ttt gac tcg att tat tgg aaa aag gcg    1756
Val Ile Lys Tyr Pro Thr Lys Phe Asp Ser Ile Tyr Trp Lys Lys Ala
205             210             215             220 cta aaa ttt cct ttg caa tct cgt cat ccc tca tta ccg acg gac cgc    1804
Leu Lys Phe Pro Leu Gln Ser Arg His Pro Ser Leu Pro Thr Asp Arg
                225             230             235 att cga acc acg ttc gtt ttc acc caa tcc gaa att aag aaa ttg aag    1852
Ile Arg Thr Thr Phe Val Phe Thr Gln Ser Glu Ile Lys Lys Leu Lys
            240             245             250 ggt tcg att cag tcc aga gtt cca agt tta gtc cat ctc tca tct ttt    1900
Gly Ser Ile Gln Ser Arg Val Pro Ser Leu Val His Leu Ser Ser Phe
        255             260             265 gta gcg att gca gct tat atg tgg gct ggc gta acg aaa tca ctc aca    1948
Val Ala Ile Ala Ala Tyr Met Trp Ala Gly Val Thr Lys Ser Leu Thr
    270             275             280 gca gat gaa gac cac gac gac ggg gat gca ttt ttc ttg att ccg gtc    1996
Ala Asp Glu Asp His Asp Asp Gly Asp Ala Phe Phe Leu Ile Pro Val
285             290             295             300 gat cta agg cca cga tta gat ccg cca gtt ccc gaa aat tac ttc ggg    2044
Asp Leu Arg Pro Arg Leu Asp Pro Pro Val Pro Glu Asn Tyr Phe Gly
                305             310             315 aac tgc tta tcg tac gcg ctg ccg aga atg cgg cgg cga gag ctg gtg    2092
Asn Cys Leu Ser Tyr Ala Leu Pro Arg Met Arg Arg Arg Glu Leu Val
            320             325             330 gga gag aaa ggg gtg ttt ctg gcg gct gag gca atc gcg gcg gag atc    2140
Gly Glu Lys Gly Val Phe Leu Ala Ala Glu Ala Ile Ala Ala Glu Ile
        335             340             345
```

```
aaa aaa agg atc aac gac aag aga ata tta gaa acg gtg gag aaa tgg       2188
Lys Lys Arg Ile Asn Asp Lys Arg Ile Leu Glu Thr Val Glu Lys Trp
     350                 355                 360 tcg ctg gag att cgt gaa gcg ttg cag aaa tca tat ttt tcg gtg gca       2236
Ser Leu Glu Ile Arg Glu Ala Leu Gln Lys Ser Tyr Phe Ser Val Ala
365                 370                 375                 380 gga tcg agc aag cta gat ctt tac ggt gca gat ttt gga tgg ggg aag       2284
Gly Ser Ser Lys Leu Asp Leu Tyr Gly Ala Asp Phe Gly Trp Gly Lys
                385                 390                 395 gcg aga aag caa gaa ata ttg tcg att gat ggg gag aaa tat gca atg       2332
Ala Arg Lys Gln Glu Ile Leu Ser Ile Asp Gly Glu Lys Tyr Ala Met
            400                 405                 410 acg ctt tgt aaa gcc agg gat ttc gaa gga gga ttg gag gtt tgc ttg       2380
Thr Leu Cys Lys Ala Arg Asp Phe Glu Gly Gly Leu Glu Val Cys Leu
        415                 420                 425 tct ttg cct aag gac aaa atg gat gct ttt gct gct tat ttt tca gcg       2428
Ser Leu Pro Lys Asp Lys Met Asp Ala Phe Ala Ala Tyr Phe Ser Ala
    430                 435                 440 gga att aat ggt taa taaatgtatg taattaaact aatattatta tgtaacaatt       2483
Gly Ile Asn Gly
445 aattaagtgt tgagtaacgt gaagaataat atcttttacc tattatatat ttatgagttg    2543 gttcaaataa aatcacttca tttattgtat taaccgttta gtgttcttct caccatattt    2603 tggtgctatt ttttaaaaaa tgtttttttt attgtatttt agtattaatt gttttaccac    2663 taaaattaca gtaaaatgca agatagttta attttacat  ttacatatga aacacattct    2723 ctttataacc aacctctcta tatatataat atgtgtgtat gtatgtatac acatgtatga    2783 atactagaaa tatatcttaa accatccatc cttcaaaaat ttcggggcca tattgcatgg    2843 tgacattata atatttgata atttcttcga acacgttatt aattcaattt ataattcta    2903 ataaaaagac gctcagacaa tatatgtaga taggatcggc ccaaagggt  gtctgggtgg    2963 gctgtcgccc atgggccccg aaatcttagg ggcaaaaaaa aaaaaattca ttatacctag    3023 ggcaaaaaaa ttaccgctct tcacttctct gcctctctcc ctcatccctc gttcctcctc    3083 tctcttccct atgtacgcct cttcactcc  ctccccctct ctcagttctc tatcacttgt    3143 attttgtatt gaaacttgt  tgaaaactaa accaaaaata gaaaaaggta tagaaaattt    3203 gaaaacaaag gttgtttttt tgtgttgctg cagttcccaa acttgccgag ttgccgactt    3263 gccgtgttga attgttatat atgttaaaag cctaaaatat atccttcag  aattgagatg    3323 gattgttgta actatcaggt ttttttttatt gagaattta  gatcaattag ttatcttgta    3383 attttttatt ctttttaata caatactccc tccatcccaa tagcaaggtc cccttgctat    3443 tgggcacggg tattaaggag gaggattatt ataatgaaaa ttaatataaa gtaagtggat    3503 tccacttttat taaggaatat tataatcaaa agtaatataa agtaagtgga ttccacttta    3563 attaggacac taattatttt cttttttggt atgagacttt gctattggga catcccaaaa    3623 aggcaaaaga gaccttgcta ttaggacggt ggacgtgctg ccgaggcacg caaattaatt    3683 tacctttcct cttctatact aactcgtagt agcggcgagt aaaggtcgaa ccctcaagga    3743 gcaattgaac tagatgtgct attagaaata aaataaacac aagtgagagg ggagtttttg    3803 gtttcaattt aactaaaaact aattatgaaa atgaaaaaac aaatataaaa cataaacagg    3863 tagacgaaat atgataaaga tagaattcta gttctcggtt cagttatcac ctttctccaa    3923 gtatttcatg aataatgcaa cgcctctttt catacaactt agaatcgatg tccaaaggtt    3983
```

```
aatatcaagc tttatttacc taattgtctc gtacgattag ttaactaaaa caagctcttt    4043
aattaactct actcaattag ataacctaga ataagctctc taga                     4087
```

<210> SEQ ID NO 3
<211> LENGTH: 448
<212> TYPE: PRT
<213> ORGANISM: Perilla frutescens

<400> SEQUENCE: 3

```
Met Thr Thr Thr Val Ile Glu Thr Cys Arg Val Gly Pro Pro Asp
1               5                   10                  15

Ser Val Ala Glu Gln Ser Leu Pro Leu Thr Phe Phe Asp Met Thr Trp
            20                  25                  30

Leu His Phe His Pro Met Leu Gln Leu Leu Phe Tyr Glu Phe Pro Cys
        35                  40                  45

Ser Lys Gln His Phe Ser Glu Ser Ile Ile Pro Lys Leu Lys Gln Ser
    50                  55                  60

Leu Ser Lys Thr Leu Ile His Phe Phe Pro Leu Ser Cys Asn Leu Ile
65                  70                  75                  80

Tyr Pro Ser Ser Pro Glu Lys Met Pro Glu Phe Arg Tyr Leu Ser Gly
                85                  90                  95

Asp Ser Val Ser Phe Thr Ile Ala Glu Ser Ser Asp Asp Phe Asp Asp
            100                 105                 110

Leu Val Gly Asn Arg Ala Glu Ser Pro Val Arg Leu Tyr Asn Phe Val
        115                 120                 125

Pro Lys Leu Pro Gln Ile Val Glu Glu Ser Asp Arg Lys Leu Phe Gln
    130                 135                 140

Val Phe Ala Val Gln Val Thr Leu Phe Pro Gly Arg Gly Val Gly Ile
145                 150                 155                 160

Gly Ile Ala Thr His His Thr Val Ser Asp Ala Pro Ser Phe Leu Ala
                165                 170                 175

Phe Ile Thr Ala Trp Ala Trp Met Ser Lys His Ile Glu Asp Glu Asp
            180                 185                 190

Glu Glu Phe Lys Ser Leu Pro Val Phe Asp Arg Ser Val Ile Lys Tyr
        195                 200                 205

Pro Thr Lys Phe Asp Ser Ile Tyr Trp Lys Lys Ala Leu Lys Phe Pro
    210                 215                 220

Leu Gln Ser Arg His Pro Ser Leu Pro Thr Asp Arg Ile Arg Thr Thr
225                 230                 235                 240

Phe Val Phe Thr Gln Ser Glu Ile Lys Lys Leu Lys Gly Ser Ile Gln
                245                 250                 255

Ser Arg Val Pro Ser Leu Val His Leu Ser Ser Phe Val Ala Ile Ala
            260                 265                 270

Ala Tyr Met Trp Ala Gly Val Thr Lys Ser Leu Thr Ala Asp Glu Asp
        275                 280                 285

His Asp Asp Gly Asp Ala Phe Phe Leu Ile Pro Val Asp Leu Arg Pro
    290                 295                 300

Arg Leu Asp Pro Pro Val Pro Glu Asn Tyr Phe Gly Asn Cys Leu Ser
305                 310                 315                 320

Tyr Ala Leu Pro Arg Met Arg Arg Arg Glu Leu Val Gly Glu Lys Gly
                325                 330                 335

Val Phe Leu Ala Ala Glu Ala Ile Ala Ala Glu Ile Lys Lys Arg Ile
            340                 345                 350

Asn Asp Lys Arg Ile Leu Glu Thr Val Glu Lys Trp Ser Leu Glu Ile
        355                 360                 365
```

```
Arg Glu Ala Leu Gln Lys Ser Tyr Phe Ser Val Ala Gly Ser Ser Lys
        370                 375                 380

Leu Asp Leu Tyr Gly Ala Asp Phe Gly Trp Gly Lys Ala Arg Lys Gln
385                 390                 395                 400

Glu Ile Leu Ser Ile Asp Gly Glu Lys Tyr Ala Met Thr Leu Cys Lys
                405                 410                 415

Ala Arg Asp Phe Glu Gly Gly Leu Glu Val Cys Leu Ser Leu Pro Lys
            420                 425                 430

Asp Lys Met Asp Ala Phe Ala Ala Tyr Phe Ser Ala Gly Ile Asn Gly
            435                 440                 445

<210> SEQ ID NO 4
<211> LENGTH: 6835
<212> TYPE: DNA
<213> ORGANISM: Perilla frutescens
<220> FEATURE:
<221> NAME/KEY: CDS
<222> LOCATION: (1608)..(2330)
<223> OTHER INFORMATION: Other ORF
<220> FEATURE:
<221> NAME/KEY: CDS
<222> LOCATION: (3439)..(4785)
<223> OTHER INFORMATION: SAT208 ORF
<220> FEATURE:
<221> NAME/KEY: misc_feature
<222> LOCATION: (6815)..(6815)
<223> OTHER INFORMATION: n is a, c, g, or t

<400> SEQUENCE: 4
```

| | | | | | |
|---|---|---|---|---|---|
| ccccaaaaac | cttgattagg | gtgatggttc | acgtagtggg | ccatcgccct | gatagacggt | 60 |
| ttttcgccct | tgacgttgg | agtccacgtt | ctttaatagt | ggactcttgt | tccaaactgg | 120 |
| aacaacactc | aaccctatct | cggtctattc | ttttgattta | taagggattt | tgccgatttc | 180 |
| ggcctattgg | ttaaaaaaat | gagctgattt | aacaaaaatt | taacgcgaat | tttaacaaaa | 240 |
| tattaacgct | tacaatttcc | attcgccatt | caggctgcgc | aactgttggg | aagggcgatc | 300 |
| ggtgcgggcc | tcttcgctat | tacgccagct | ggcgaaaggg | ggatgtgctg | caaggcgatt | 360 |
| aagttgggta | acgccagggt | ttcccagtc | acgacgttgt | aaaacgacgg | ccagtgagcg | 420 |
| cgcgtaatac | gactcactat | agggcgaatt | gggtaccggg | cccccctcg | aggtcgacgg | 480 |
| tatcgataag | cttgatatcg | aattcctgca | gcccggggga | tccactagtt | ctagaagatg | 540 |
| aagagacaaa | acatcgacta | cttgcccttg | tgtttgggca | aaattaaatt | aatgtaattg | 600 |
| taattgtgag | atgtgtgtta | gtaattatgc | tatgtgtgtg | ttagtaatta | tgagatgtgt | 660 |
| gtgtttgtaa | ttttgagatg | tcttttcctc | actttataaa | taattaatgt | attttatgca | 720 |
| tatctatttc | tcttattctt | ttcatacaaa | cctgcatgca | taagtctcaa | tcatgcattg | 780 |
| gattctttat | gccttgtcaa | tttcttttg | tacaaacctc | atgcatctca | atcatgcatt | 840 |
| ggattcttat | actctcattt | caatttatat | gcaagagtaa | agctaagtat | atcacatgca | 900 |
| ttggattcca | ctttatatca | aattgatttc | ttgataaatc | acatgctttt | gtcagccatc | 960 |
| acatgcattg | gattccactt | tatatcaaat | taatttcttg | ataaatcaca | tactttgtc | 1020 |
| ggccatttca | tgcattggat | tccactttat | atcaaattga | ttttttgata | aatcacatgc | 1080 |
| ttttgtcggc | tagccatgc | tttgtctata | catatctcag | aaaatgcaca | tcaaagaaa | 1140 |
| ctcaaacaaa | atcctcaata | ccttaccaca | tctttcaact | tcactttaga | aaaatgtctg | 1200 |
| cacatgaaaa | ttctgatgtt | gaatcaaact | caagttctaa | ttattctgat | tctaacgaac | 1260 |
| ttgatgaatg | gctagagcga | ggttatgaaa | aatatcgtga | agttgatagt | ataatccaga | 1320 |
| atgtgctcat | aaataatccc | aatctggttg | taggagctca | aacttctaca | gtcagaagaa | 1380 |

```
                                                                -continued ggtattgtga tagggaacgt gagaatggtg aagagcgttt gatgaaagac tatttttgtct   1440 ctaatccaac gtattctcca gagctcttcc gacgatgatt tcacatgcag aaatcacttt   1500
ttcttcgtat agtggaggcc gttactacca atgatgacta ttttcaacag aggccaaatt   1560
gcacgggtag aaaaggtctt tcaccattgt aaaaatgtac aggagct atg agg gta     1616
                                                 Met Arg Val
                                                  1 ttg gct tat ggg gca tca gcc gat gtc gtt gat gaa tac tta cga atg     1664
Leu Ala Tyr Gly Ala Ser Ala Asp Val Val Asp Glu Tyr Leu Arg Met
        5                  10                  15 agt gca acg gta aca aga gat gct gtc atc cat ttc gta gaa ggt gtc     1712
Ser Ala Thr Val Thr Arg Asp Ala Val Ile His Phe Val Glu Gly Val
 20                  25                  30                  35 att tca tgc ttc agt gac aca tat ctt agg aag cct aat caa caa gat     1760
Ile Ser Cys Phe Ser Asp Thr Tyr Leu Arg Lys Pro Asn Gln Gln Asp
                 40                  45                  50 ttg gca aga cta ctc tat gtt gga gag caa cgt ggt ttt cct ggc atg     1808
Leu Ala Arg Leu Leu Tyr Val Gly Glu Gln Arg Gly Phe Pro Gly Met
             55                  60                  65 att ggt agt att gat tgc atg cac tgg gaa tgg aca aat tgt cct aat     1856
Ile Gly Ser Ile Asp Cys Met His Trp Glu Trp Thr Asn Cys Pro Asn
         70                  75                  80 gcc tgg gca ggg caa ttt aca ggg aga agt gga aag tca aca atc att     1904
Ala Trp Ala Gly Gln Phe Thr Gly Arg Ser Gly Lys Ser Thr Ile Ile
 85                  90                  95 ttg gaa gct gtt gca tca tat gat tta tgg ata tgg cat gcg ttt ttt     1952
Leu Glu Ala Val Ala Ser Tyr Asp Leu Trp Ile Trp His Ala Phe Phe
100                 105                 110                 115 gga aca tca ggt gcg tgc aat gat att aat gtt ctc cac ggt tct cca     2000
Gly Thr Ser Gly Ala Cys Asn Asp Ile Asn Val Leu His Gly Ser Pro
                120                 125                 130 att ttt agt gat gtt tta gaa ggt cga gca cca cat gtt agt tac atc     2048
Ile Phe Ser Asp Val Leu Glu Gly Arg Ala Pro His Val Ser Tyr Ile
            135                 140                 145 gtc aat ggt cgc caa aat gat aga gca tat tat ctc acc gat ggc ata     2096
Val Asn Gly Arg Gln Asn Asp Arg Ala Tyr Tyr Leu Thr Asp Gly Ile
        150                 155                 160 tat cct tca tgg gct gca ttt gta aag tca atc aca tct cct atg act     2144
Tyr Pro Ser Trp Ala Ala Phe Val Lys Ser Ile Thr Ser Pro Met Thr
165                 170                 175 cga aag tat aag ttg ttt gtt caa cac caa gaa gct gct aga aaa gat     2192
Arg Lys Tyr Lys Leu Phe Val Gln His Gln Glu Ala Ala Arg Lys Asp
180                 185                 190                 195 gta gaa cgg gcc ttt gga gtt cta caa gct cgt ttt gca ttt att cga     2240
Val Glu Arg Ala Phe Gly Val Leu Gln Ala Arg Phe Ala Phe Ile Arg
                200                 205                 210 cgt cca tgt ctt gtt tgg gac aag gtt ttg atg gga aaa att atg atg     2288
Arg Pro Cys Leu Val Trp Asp Lys Val Leu Met Gly Lys Ile Met Met
            215                 220                 225 gct tgt atc atc ata cac aat atg att gtg gag gat gaa tga             2330
Ala Cys Ile Ile Ile His Asn Met Ile Val Glu Asp Glu
        230                 235                 240 gacacatacc taaactatta tgatcccaca gagttttga cagatgagtc ttcaggagga   2390
gatgctgaac cttttcacta ctctactgaa cgcatcacaa gttatcggc ttatatgact   2450 aataggggatc aacttcacaa cagagaggct catagagctc ttaaagagga tttgatcgag  2510
cacatatgga aaaaattcgg cactaactaa atatataatt tacgttttat gcactcgtaa   2570
tttaaaattt catgtgtctc attgtagttt atttaattat gttttcactc ttgtaatttt   2630
```

```
tatttttgttg tgaagtaaat tatgaatttta taattatatg ggtaattttt tgataattat   2690
gcaattaaaa ataattaata ttttttaaat gcaagagaaa aatgttattt taataacatg   2750
ttcttattaa aaaataaaat gataaatatt ttatgtaggt tgggagaaaa tgaaaaaata   2810
atattttatt tgaaggttgg gttggatgag gtcactgatg ggagtataaa taatactccc   2870
tccgtcccat aattattgtc cattattcct ttttgggatg tcccaaaatt atagtcctat   2930
tctaaattgg gattgtattt aaatattctt ttacaaatat aaccctattt gatatagtat   2990
gaatgcaatt aatatagtaa aaaaataagg gcaatatagg ataattattg taaattgtat   3050
atttccaata catattaaat gtgatttctt aatctgtgtg aaaataggaa gtggactata   3110
attatgggac ggagggagta taaagttgga ggttgtggat gtggaggaga aagaaattaa   3170
tattttattt aaagattgga ttaaaggagg tcactgatgt gggtagtctt agaggaaatg   3230
tagtcttaga ggaaatctgc ccagcaaaat aaaataataa gtaaataaat aaactaaata   3290
tgtattgaat gcgacatcta gcaatatagc cacatatata gtgcagtagc acgcagcgct   3350
cgttactcgt cagtcgtcaa agaatggtaa gtatagaaaa gcatctttaa ataacacacc   3410
aaaaaccaca gctacgttca acaccgcc atg acc acc acc gtg atc gaa acg       3462
                                Met Thr Thr Thr Val Ile Glu Thr
                                                    245 tgt aga gtt ggg cca ccg ccg gac tcg gtg gcg gag caa tcg ttg ccg       3510
Cys Arg Val Gly Pro Pro Pro Asp Ser Val Ala Glu Gln Ser Leu Pro
    250             255                 260 ctc aca ttc ttc gac atg acg tgg ctg cat ttt cat ccc atg ctt cag       3558
Leu Thr Phe Phe Asp Met Thr Trp Leu His Phe His Pro Met Leu Gln
265             270                 275                 280 ctc ctc ttc tac gaa ttc cct tgt tcc aag caa cat ttc tca gaa tcc       3606
Leu Leu Phe Tyr Glu Phe Pro Cys Ser Lys Gln His Phe Ser Glu Ser
                285                 290                 295 atc att cca aaa ctc aaa caa tct ctc tct aaa act ctc ata cac ttc       3654
Ile Ile Pro Lys Leu Lys Gln Ser Leu Ser Lys Thr Leu Ile His Phe
            300                 305                 310 ttc cct ctc tca tgc aat tta atc tac cct tca tct ccg gag aaa atg       3702
Phe Pro Leu Ser Cys Asn Leu Ile Tyr Pro Ser Ser Pro Glu Lys Met
        315                 320                 325 ccc gag ttt cgg tat cta tcg ggg gac tcg gtt tct ttc act atc gca       3750
Pro Glu Phe Arg Tyr Leu Ser Gly Asp Ser Val Ser Phe Thr Ile Ala
    330                 335                 340 gaa tct agc gac gac ttc gat gat ctc gtc gga aat cgc gca gaa tct       3798
Glu Ser Ser Asp Asp Phe Asp Asp Leu Val Gly Asn Arg Ala Glu Ser
345                 350                 355                 360 ccc gtt agg ctc tac aac ttc gtc cct aaa ttg ccg cag att gtc gaa       3846
Pro Val Arg Leu Tyr Asn Phe Val Pro Lys Leu Pro Gln Ile Val Glu
                365                 370                 375 gaa tct gat aga aaa ctc ttc caa gtt ttc gcc gtg cag gtg act ctt       3894
Glu Ser Asp Arg Lys Leu Phe Gln Val Phe Ala Val Gln Val Thr Leu
            380                 385                 390 ttc cca ggt cga ggc gtc ggt att gga ata gca acg cat cac acc gtt       3942
Phe Pro Gly Arg Gly Val Gly Ile Gly Ile Ala Thr His His Thr Val
        395                 400                 405 agc gat gcc ccg tcg ttt ctc gcc ttt ata acg gct tgg gct tgg atg       3990
Ser Asp Ala Pro Ser Phe Leu Ala Phe Ile Thr Ala Trp Ala Trp Met
    410                 415                 420 agc aaa cac att gaa gat gaa gat gaa gag ttt aaa tct ttg cca gtt       4038
Ser Lys His Ile Glu Asp Glu Asp Glu Glu Phe Lys Ser Leu Pro Val
425                 430                 435                 440
```

| | |
|---|---|
| ttc gat aga tcc gtc ata aaa tat ccg acg aaa ttt gac tcg att tat<br>Phe Asp Arg Ser Val Ile Lys Tyr Pro Thr Lys Phe Asp Ser Ile Tyr<br>445 450 455 | 4086 |
| tgg aaa aag gcg cta aaa ttt cct ttg caa tct cgt cat ccc tca tta<br>Trp Lys Lys Ala Leu Lys Phe Pro Leu Gln Ser Arg His Pro Ser Leu<br>460 465 470 | 4134 |
| ccg acg gac cgc att cga acc acg ttc gtt ttc acc caa tcc gaa att<br>Pro Thr Asp Arg Ile Arg Thr Thr Phe Val Phe Thr Gln Ser Glu Ile<br>475 480 485 | 4182 |
| aag aaa ttg aag ggt tcg att cag tcc aga gtt cca agt tta gtc cat<br>Lys Lys Leu Lys Gly Ser Ile Gln Ser Arg Val Pro Ser Leu Val His<br>490 495 500 | 4230 |
| ctc tca tct ttt gta gcg att gca gct tat atg tgg gct ggc gta acg<br>Leu Ser Ser Phe Val Ala Ile Ala Ala Tyr Met Trp Ala Gly Val Thr<br>505 510 515 520 | 4278 |
| aaa tca ctc aca gca gat gaa gac cac gac gac ggg gat gca ttt ttc<br>Lys Ser Leu Thr Ala Asp Glu Asp His Asp Asp Gly Asp Ala Phe Phe<br>525 530 535 | 4326 |
| ttg att ccg gtc gat cta agg cca cga tta gat ccg cca gtt ccc gaa<br>Leu Ile Pro Val Asp Leu Arg Pro Arg Leu Asp Pro Pro Val Pro Glu<br>540 545 550 | 4374 |
| aat tac ttc ggg aac tgc tta tcg tac gcg ctg ccc aga atg cgg cgg<br>Asn Tyr Phe Gly Asn Cys Leu Ser Tyr Ala Leu Pro Arg Met Arg Arg<br>555 560 565 | 4422 |
| cga gag ctg gtg gga gag aaa ggg gtg ttt ctg gcg gct gag gca atc<br>Arg Glu Leu Val Gly Glu Lys Gly Val Phe Leu Ala Ala Glu Ala Ile<br>570 575 580 | 4470 |
| gcg gcg gag atc aaa aaa agg atc aac gac aag aga ata tta gaa acg<br>Ala Ala Glu Ile Lys Lys Arg Ile Asn Asp Lys Arg Ile Leu Glu Thr<br>585 590 595 600 | 4518 |
| gtg gag aaa tgg tcg ctg gag att cgt gaa gcg ttg cag aaa tca tat<br>Val Glu Lys Trp Ser Leu Glu Ile Arg Glu Ala Leu Gln Lys Ser Tyr<br>605 610 615 | 4566 |
| ttt tcg gtg gca gga tcg agc aag cta gat ctt tac ggt gca gat ttt<br>Phe Ser Val Ala Gly Ser Ser Lys Leu Asp Leu Tyr Gly Ala Asp Phe<br>620 625 630 | 4614 |
| gga tgg ggg aag gcg aga aag caa gaa ata ttg tcg att gat ggg gag<br>Gly Trp Gly Lys Ala Arg Lys Gln Glu Ile Leu Ser Ile Asp Gly Glu<br>635 640 645 | 4662 |
| aaa tat gca atg acg ctt tgt aaa gcc agg gat ttc gaa gga gga ttg<br>Lys Tyr Ala Met Thr Leu Cys Lys Ala Arg Asp Phe Glu Gly Gly Leu<br>650 655 660 | 4710 |
| gag gtt tgc ttg tct ttg cct aag gac aaa atg gat gct ttt gct gct<br>Glu Val Cys Leu Ser Leu Pro Lys Asp Lys Met Asp Ala Phe Ala Ala<br>665 670 675 680 | 4758 |
| tat ttt tca gcg gga att aat ggt taa taaatgtatg taattaaact<br>Tyr Phe Ser Ala Gly Ile Asn Gly<br>685 | 4805 |
| aatattatta tgtaacaatt aattaagtgt tgagtaacgt gaagaataat atcttttacc | 4865 |
| tattatatat ttatgagttg gttcaaataa aatcacttca tttattgtat taaccgttta | 4925 |
| gtgttcttct caccatattt tggtgctatt ttttaaaaaa tgtttttttt attgtatttt | 4985 |
| agtattaatt gttttaccac taaaattaca gtaaaatgca agatagttta attttttacat | 5045 |
| ttacatatga aacacattct ctttataacc aacctctcta tatataat atgtgtgtat | 5105 |
| gtatgtatac acatgtatga atactagaaa tatatcttaa accatccatc cttcaaaaat | 5165 |
| ttcggggcca tattgcatgg tgacattata atatttgata atttcttcga acacgttatt | 5225 |
| aattcaattt aataattcta ataaaaagac gctcagacaa tatatgtaga taggatcggc | 5285 |

```
ccaaaggggt gtctgggtgg gctgtcgccc atgggccccg aaatcttagg ggcaaaaaaa    5345
aaaaaattca ttatacctag ggcaaaaaaa ttaccgctct tcacttctct gcctctctcc    5405
ctcatccctc gttcctcctc tctcttccct atgtacgcct ctttcactcc ctccccctct    5465
ctcagttctc tatcacttgt attttgtatt gaaaacttgt tgaaaactaa accaaaaata    5525 gaaaaggta tagaaaattt gaaaacaaag gttgtttttt tgtgttgctg cagttcccaa     5585
acttgccgag ttgccgactt gccgtgttga attgttatat atgttaaaag cctaaaatat    5645
atcctttcag aattgagatg gattgttgta actatcaggt ttttttttatt gagaatttta   5705 gatcaattag ttatcttgta attttttatt ctttttaata caatactccc tccatcccaa    5765
tagcaaggtc cccttgctat tgggcacggg tattaaggag gaggattatt ataatgaaaa    5825
ttaatataaa gtaagtggat tccactttat taaggaatat tataatcaaa agtaatataa    5885
agtaagtgga ttccactttta attaggacac taattatttt cttttttggt atgagacttt   5945
gctattggga catcccaaaa aggcaaaaga gaccttgcta ttaggacggt ggacgtgctg    6005
ccgaggcacg caaattaatt taccttcct cttctatact aactcgtagt agcggcgagt     6065
aaaggtcgaa ccctcaagga gcaattgaac tagatgtgct attagaaata aaataaacac    6125
aagtgagagg ggagttttg gtttcaattt aactaaaact aattatgaaa atgaaaaaac     6185
aaatataaaa cataaacagg tagacgaaat atgataaaga tagaattcta gttctcggtt    6245
cagttatcac ctttctccaa gtatttcatg aataatgcaa cgcctctttt catacaactt    6305
agaatcgatg tccaaaggtt aatatcaagc tttatttacc taattgtctc gtacgattag    6365
ttaactaaaa caagctcttt aattaactct actcaattag ataacctaga ataagctctc    6425
tagagcggcc gccaccgcgg tggagctcca gcttttgttc cctttagtga gggttaattg    6485
cgcgcttggc gtaatcatgg tcatagctgt ttcctgtgtg aaattgttat ccgctcacaa    6545
ttccacacaa catacgagcc ggaagcataa agtgtaaagc ctggggtgcc taatgagtga    6605
gctaactcac attaattgcg ttgcgctcac tgcccgcttt ccagtcggga aacctgtcgt    6665
gccagctgca ttaatgaatc ggccaacgcg cggggagagg cggttgcgt attgggccgc     6725 tcttccgctt ccttggttac ttgactcgct gcgctcggcc gtcggctgcg gcgagcggta    6785
tcaagctcac tcaaaggcgg taataccggn tatccacaga atcagggat              6835
```

<210> SEQ ID NO 5
<211> LENGTH: 240
<212> TYPE: PRT
<213> ORGANISM: Perilla frutescens

<400> SEQUENCE: 5

Met Arg Val Leu Ala Tyr Gly Ala Ser Ala Asp Val Val Asp Glu Tyr
1               5                   10                  15

Leu Arg Met Ser Ala Thr Val Thr Arg Asp Ala Val Ile His Phe Val
            20                  25                  30

Glu Gly Val Ile Ser Cys Phe Ser Asp Thr Tyr Leu Arg Lys Pro Asn
        35                  40                  45

Gln Gln Asp Leu Ala Arg Leu Leu Tyr Val Gly Glu Gln Arg Gly Phe
    50                  55                  60

Pro Gly Met Ile Gly Ser Ile Asp Cys Met His Trp Glu Trp Thr Asn
65                  70                  75                  80

Cys Pro Asn Ala Trp Ala Gly Gln Phe Thr Gly Arg Ser Gly Lys Ser
                85                  90                  95

Thr Ile Ile Leu Glu Ala Val Ala Ser Tyr Asp Leu Trp Ile Trp His
            100                 105                 110

```
Ala Phe Phe Gly Thr Ser Gly Ala Cys Asn Asp Ile Asn Val Leu His
        115                 120                 125

Gly Ser Pro Ile Phe Ser Asp Val Leu Glu Gly Arg Ala Pro His Val
    130                 135                 140

Ser Tyr Ile Val Asn Gly Arg Gln Asn Asp Arg Ala Tyr Tyr Leu Thr
145                 150                 155                 160

Asp Gly Ile Tyr Pro Ser Trp Ala Ala Phe Val Lys Ser Ile Thr Ser
                165                 170                 175

Pro Met Thr Arg Lys Tyr Lys Leu Phe Val Gln His Gln Glu Ala Ala
            180                 185                 190

Arg Lys Asp Val Glu Arg Ala Phe Gly Val Leu Gln Ala Arg Phe Ala
        195                 200                 205

Phe Ile Arg Arg Pro Cys Leu Val Trp Asp Lys Val Leu Met Gly Lys
    210                 215                 220

Ile Met Met Ala Cys Ile Ile His Asn Met Ile Val Glu Asp Glu
225                 230                 235                 240

<210> SEQ ID NO 6
<211> LENGTH: 448
<212> TYPE: PRT
<213> ORGANISM: Perilla frutescens

<400> SEQUENCE: 6

Met Thr Thr Thr Val Ile Glu Thr Cys Arg Val Gly Pro Pro Asp
1               5                   10                  15

Ser Val Ala Glu Gln Ser Leu Pro Leu Thr Phe Phe Asp Met Thr Trp
            20                  25                  30

Leu His Phe His Pro Met Leu Gln Leu Leu Phe Tyr Glu Phe Pro Cys
        35                  40                  45

Ser Lys Gln His Phe Ser Glu Ser Ile Ile Pro Lys Leu Lys Gln Ser
    50                  55                  60

Leu Ser Lys Thr Leu Ile His Phe Phe Pro Leu Ser Cys Asn Leu Ile
65                  70                  75                  80

Tyr Pro Ser Ser Pro Glu Lys Met Pro Glu Phe Arg Tyr Leu Ser Gly
                85                  90                  95

Asp Ser Val Ser Phe Thr Ile Ala Glu Ser Ser Asp Asp Phe Asp Asp
            100                 105                 110

Leu Val Gly Asn Arg Ala Glu Ser Pro Val Arg Leu Tyr Asn Phe Val
        115                 120                 125

Pro Lys Leu Pro Gln Ile Val Glu Glu Ser Arg Lys Leu Phe Gln
    130                 135                 140

Val Phe Ala Val Gln Val Thr Leu Phe Pro Gly Arg Gly Val Gly Ile
145                 150                 155                 160

Gly Ile Ala Thr His His Thr Val Ser Asp Ala Pro Ser Phe Leu Ala
                165                 170                 175

Phe Ile Thr Ala Trp Ala Trp Met Ser Lys His Ile Glu Asp Glu Asp
            180                 185                 190

Glu Glu Phe Lys Ser Leu Pro Val Phe Asp Arg Ser Val Ile Lys Tyr
        195                 200                 205

Pro Thr Lys Phe Asp Ser Ile Tyr Trp Lys Lys Ala Leu Lys Phe Pro
    210                 215                 220

Leu Gln Ser Arg His Pro Ser Leu Pro Thr Arg Ile Arg Thr Thr
225                 230                 235                 240

Phe Val Phe Thr Gln Ser Glu Ile Lys Lys Leu Lys Gly Ser Ile Gln
                245                 250                 255
```

```
Ser Arg Val Pro Ser Leu Val His Leu Ser Ser Phe Val Ala Ile Ala
            260             265             270

Ala Tyr Met Trp Ala Gly Val Thr Lys Ser Leu Thr Ala Asp Glu Asp
        275             280             285

His Asp Asp Gly Asp Ala Phe Phe Leu Ile Pro Val Asp Leu Arg Pro
    290             295             300

Arg Leu Asp Pro Pro Val Pro Glu Asn Tyr Phe Gly Asn Cys Leu Ser
305             310             315             320

Tyr Ala Leu Pro Arg Met Arg Arg Glu Leu Val Gly Glu Lys Gly
                325             330             335

Val Phe Leu Ala Ala Glu Ala Ile Ala Ala Glu Ile Lys Lys Arg Ile
            340             345             350

Asn Asp Lys Arg Ile Leu Glu Thr Val Glu Lys Trp Ser Leu Glu Ile
        355             360             365

Arg Glu Ala Leu Gln Lys Ser Tyr Phe Ser Val Ala Gly Ser Ser Lys
    370             375             380

Leu Asp Leu Tyr Gly Ala Asp Phe Gly Trp Gly Lys Ala Arg Lys Gln
385             390             395             400

Glu Ile Leu Ser Ile Asp Gly Glu Lys Tyr Ala Met Thr Leu Cys Lys
            405             410             415

Ala Arg Asp Phe Glu Gly Gly Leu Glu Val Cys Leu Ser Leu Pro Lys
        420             425             430

Asp Lys Met Asp Ala Phe Ala Ala Tyr Phe Ser Ala Gly Ile Asn Gly
    435             440             445

<210> SEQ ID NO 7
<211> LENGTH: 27
<212> TYPE: DNA
<213> ORGANISM: Artificial
<220> FEATURE:
<223> OTHER INFORMATION: HindIII containing primer

<400> SEQUENCE: 7
aagcttaact attatgatcc cacagag                                    27

<210> SEQ ID NO 8
<211> LENGTH: 24
<212> TYPE: DNA
<213> ORGANISM: Artificial
<220> FEATURE:
<223> OTHER INFORMATION: BamHI containing primer

<400> SEQUENCE: 8
ggatccggcg gtgttgaacg tagc                                       24
```

PERILLA-DERIVED PROMOTER FUNCTIONING IN PETALS

CROSS REFERENCE TO RELATED APPLICATIONS

This application is the National Stage of International Application No. PCT/JP2010/053886 filed Mar. 9, 2010, and claims benefit of Japanese Patent Application No. 2009-107057 filed Apr. 24, 2009, which are herein incorporated by reference in their entirety.

REFERENCE TO A SEQUENCE LISTING

A Sequence Listing containing SEQ ID NOS: 1-8 is incorporated herein by reference.

TECHNICAL FIELD

The present invention relates to a novel promoter. More particularly, the present invention relates to a transcriptional regulatory region of perilla-derived anthocyanin 3-acyltransferase (3AT) gene and to the use thereof.

BACKGROUND ART

The use of genetic recombination technology makes it possible to impart new traits to plants by expressing a useful gene in a target plant. A wide range of genetically modified plants produced in this manner have already been cultivated. Since regulation of gene expression is mainly controlled at the level of transcription, transcriptional regulation is the most important in terms of regulating the expression of genes. Namely, transcribing a gene at a suitable time, in a suitable tissue and at a suitable strength is important for producing an industrially useful genetically modified plant. In many cases, initiation of transcription is controlled by a DNA sequence on the 5'-side of a translated region, while termination is controlled by a DNA sequence on the 3'-side of a transcribed region. A region of DNA that determines the starting site of gene transcription and directly regulates the frequency thereof is referred to as a promoter, while the region that determines termination of transcription is referred to as a terminator. A promoter is located several tens of base pairs (bp) from the 5'-side of an initiation codon, and frequently contains a TATA box and the like. A cis element that binds various transcriptional regulatory factors is also present on the 5'-side, and the presence thereof serves to control the timing of transcription, the tissue in which transcription takes place and transcriptional strength. Transcriptional regulatory factors are classified into many families according to their amino acid sequence. For example, examples of well-known families of transcriptional regulatory factors include Myb type transcriptional regulatory factors and bHLH (basic helix loop helix) type transcriptional regulatory factors. In actuality, the terms transcriptional regulatory factor and promoter are frequently used with the same meaning and are not strictly distinguished.

Anthocyanins, which compose the main components of flower color, are a member of secondary metabolites generically referred to as flavonoids. The color of anthocyanins is dependent on their structure. Namely, color becomes blue as the number of hydroxyl groups of the B ring of anthocyanidins, which is the chromophores of anthocyanins, increases. In addition, as the number of aromatic acyl groups (such as coumaroyl groups or caffeolyl groups) that modify the anthocyanin increases, the color of the anthocyanin becomes blue (namely, the wavelength of maximum absorbance shifts to a longer wavelength) and the stability of the anthocyanin is known to increase (see Non-Patent Document 1).

Considerable research has been conducted on those enzymes and genes that encode those enzymes involved in the biosynthesis of anthocyanins (see, Non-Patent Document 1). For example, an enzyme gene that catalyzes a reaction by which an aromatic acyl group is transferred to anthocyanin is obtained from Japanese gentian, lavender and petunias (see Patent Document 1 and Patent Document 2). Several enzyme genes involved in the synthesis of anthocyanin that accumulates in the leaves of perilla (malonylcyanin, 3-O-(6-O-(E)-p-coumaroyl-β-D-glucopyranosyl)-5-O-(6-O-malonyl-β-D-glucopyranosyl)-cyanidin) (see Non-Patent Document 2) have previously been reported, including human hydroxycinnamoyl CoA: anthocyanin-3-glucoside-aromatic acyl transferase (3AT) gene (or more simply referred to as "perilla anthocyanin-3-acyl transferase (3AT) gene") (see Patent Document 1). Moreover, findings have also been obtained regarding the transcriptional regulation of biosynthetic genes of anthocyanins. Cis element sequences bound by Myb type transcriptional regulatory factor and bHLH type transcriptional regulatory factor are present in the transcriptional regulatory region located on the 5'-side of the initiation codons of these genes. Myb type transcriptional regulatory factor and bHLH type transcriptional regulatory factor are known to control synthesis of anthocyanins in petunia, maize and perilla (see Non-Patent Document 1).

Promoters (also referred to as transcriptional regulatory regions) responsible for gene transcription in plants consist of so-called constitutive promoters, which function in any tissue and at any time such as in the developmental stage, organ/tissue-specific promoters, which only function in specific organs and tissues, and time-specific promoters, which only express genes at a specific time in the developmental stage. Constitutive promoters are frequently used as promoters for expressing useful genes in genetically modified plants. Typical examples of constitutive promoters include cauliflower mosaic virus 35S promoter (to also be abbreviated as CaMV35S) and promoters constructed on the basis thereof (see Non-Patent Document 3), and Mad promoter (see Non-Patent Document 4). In plants, however, many genes are only expressed in specific tissues or organs or are only expressed at specific times. This suggests that tissue/organ-specific or time-specific expression of genes is necessary for plants. There are examples of genetic recombination of plants that utilize such tissue/organ-specific or time-specific transcriptional regulatory regions. For example, there are examples of protein being accumulated in seeds by using a seed-specific transcriptional regulatory region.

However, although plants produce flowers of various colors, there are few species capable of producing flowers of all colors due to genetic restrictions on that species. For example, there are no varieties of rose or carnation in nature that are capable of producing blue or purple flowers. This is because roses and carnations lack the flavonoid 3',5'-hydroxylase (hereinafter simply referred to as F3'5'H) gene required to synthesize the anthocyanin, delphinidin, which is synthesized by many species that produce blue and purple flowers. These species can be made to produce blue flowers by transforming with the F3'5'H gene of petunia or pansy, for example, which are species capable of producing blue and purple flowers. In this case, the transcriptional regulatory region of chalcone synthase gene derived from snapdragon or petunia is used to transcribe F3'5'H gene derived from a different species. Examples of plasmids containing the transcriptional regulatory region of chalcone synthase gene derived from snapdragon or petunia include plasmids pCGP485 and pCGP653 described in Patent Document 3, and examples of plasmids containing a constitutive transcriptional regulatory region include plasmid PCGP628 (containing a Mad promoter) and plasmid pSPB130 (containing a CaMV35S promoter to which is added EI2 enhancer) described in Patent Document 4.

However, it is difficult to predict how strongly such promoters function in recombinant plants to be able to bring about a target phenotype. In addition, transforming a plant with the same or similar base sequence, creating numerous copies of a introduced gene in chromosomes or repeatedly inserting a transgene may cause gene silencing (see Non-Patent Document 5). Thus, since repeatedly using the same promoter to express a plurality of exogenous genes may cause gene silencing, this should be avoided.

On the basis of the above, although several promoters have been used to alter flower color, a promoter is still required that is useful for changing to other flower colors corresponding to the host plant.

PRIOR ART DOCUMENTS

Patent Documents

Patent Document 1: WO 96/25500
Patent Document 2: WO 01/72984
Patent Document 3: WO 94/28140
Patent Document 4: WO 05/17147

Non-Patent Documents

Non-Patent Document 1: Plant J., 54, 737-749, 2008
Non-Patent Document 2: Agricultural and Biological Chemistry, 53, 797-800, 1989
Non-Patent Document 3: Plant Cell Physiology, 37, 49-59, 1996
Non-Patent Document 4: Plant Molecular Biology, 15, 373-381, 1990
Non-Patent Document 5: Annals of Botany, 79, 3-12, 1997

SUMMARY OF THE INVENTION

Problems to be Solved by the Invention

An object of the present invention is to provide a novel promoter useful for altering flower color of plants.

In the case of expressing an exogenous gene in a plant, preferably in a specific organ or tissue, and more preferably in an organ or petal in which anthocyanin accumulates, it is desirable to select a suitable promoter and terminator. Thus, another object of the present invention is to acquire such a sequence.

Means for Solving the Problems

As a result of conducting extensive studies and experiments to solve the aforementioned problems, the inventors of the present invention found and confirmed the usefulness of a transcriptional regulatory region of perilla-derived anthocyanin 3-acyltransferase (3AT) gene as a novel promoter that is useful for altering the flower color of plants, thereby leading to completion of the present invention.

Namely, the present invention is as described below.

[1] A nucleic acid selected from the group consisting of:
(1) a nucleic acid containing the nucleotide sequence indicated in SEQ ID NO. 1;
(2) a nucleic acid able to function as a transcriptional regulatory region of perilla anthocyanin 3-acyltransferase, and containing a nucleotide sequence in which the nucleotide sequence indicated in SEQ ID NO. 1 has been modified by addition, deletion and/or substitution of one or several nucleotides;
(3) a nucleic acid able to function as a transcriptional regulatory region of perilla anthocyanin 3-acyltransferase, and able to hybridize under high stringent conditions with a nucleic acid consisting of a nucleotide sequence complementary to the nucleotide sequence indicated in SEQ ID NO. 1; and,
(4) a nucleic acid able to function as a transcriptional regulatory region of perilla anthocyanin 3-acyltransferase, and having sequence identity of at least 90% with the nucleotide sequence indicated in SEQ ID NO. 1.

[2] An expression vector or expression cassette containing the nucleic acid described in [1] above.

[3] The expression vector or expression cassette described in [2] above, containing the nucleotide sequence indicated in SEQ ID NO. 2.

[4] A non-human host other than chrysanthemum transformed by the expression vector or expression cassette described in [2] or [3] above.

[5] A plant other than chrysanthemum, progeny thereof, or vegetative proliferation product, part or tissue thereof, transformed with the nucleic acid described in [1] above.

[6] The plant other than chrysanthemum, progeny thereof, or vegetative proliferation product, part or tissue thereof described in [5] above, which is a cut flower.

[7] A cut flower processed product using the cut flower described in [6] above.

Effects of the Invention

A promoter region thought to govern transcription of an enzyme gene in perilla leaves, namely a transcriptional regulatory region of perilla anthocyanin 3-acyltransferase, was determined to be able to function as a transcriptional regulatory region in the petals of different species of plants in the form of petunias and roses. Thus, transcription of an exogenous gene can be made to specifically occur in tissues such as flowers in which anthocyanins accumulate by using the transcriptional regulatory region of perilla anthocyanin 3-acyltransferase gene. Examples of the transcribed exogenous genes include, but are not limited to, genes relating to flower color and fragrance.

EMBODIMENTS OF THE INVENTION

An example of a transcriptional regulatory region of the present invention is a nucleic acid composed of the nucleotide sequence indicated in SEQ ID NO. 1. However, a promoter composed of a nucleotide sequence in which one or several (1, 2, 3, 4, 5, 6, 7, 8, 9 or 10) nucleotides has been modified by addition, deletion and/or substitution in a nucleic acid consisting of the nucleotide sequence indicated in SEQ ID NO. 1 is also thought to maintain activity similar to that of the original promoter. Thus, the present invention also relates to a nucleic acid consisting of a nucleotide sequence modified by addition, deletion and/or substitution of one or several of nucleotides in the nucleotide sequence indicated in SEQ ID NO. 1 provided the nucleic acid is able to function as a transcriptional regulatory region in flower petals.

The present invention also relates to a nucleic acid able to function as a transcriptional regulatory region of perilla anthocyanin 3-acyltransferase gene and able to hybridize under high stringent conditions with the nucleotide sequence indicated in SEQ ID NO. 1, or a nucleic acid able to function as a transcriptional regulatory region of perilla anthocyanin 3-acyltransferase gene and has sequence identity of at least 90% with the nucleotide sequence indicated in SEQ ID NO. 1.

Examples of these nucleic acids include nucleic acids able to hybridize under high stringent conditions with a polynucleotide containing the nucleotide sequence indicated in SEQ ID NO. 1, and are consisting of nucleotide sequences having sequence identity with the nucleotide sequence indicated in SEQ ID NO. 1 of preferably about 70% or more, more preferably about 80%, 81%, 82%, 83%, 84%, 85%, 86%, 87%, 88%, 89%, 90%, 91%, 92%, 93%, 94%, 95%, 96%, 97% or 98%, and most preferably about 99%.

Here, stringent conditions refer to hybridization conditions easily determined by a person with ordinary skill in the art that are typically determined empirically dependent on probe length, washing temperature and salt concentration. In general, the temperature for suitable annealing becomes higher the longer the probe, and the temperature becomes lower the shorter the probe. Hybridization is generally dependent on the ability of denatured DNA to re-anneal in the case a complementary strand is present in an environment at a temperature close to but below the melting temperature thereof. More specifically, an example of low stringent conditions consists of washing in 0.1% SDS solution at 5×SSC under temperature conditions of 37° C. to 42° C. in the filter washing stage following hybridization. In addition, an example of high stringent conditions consists of washing in 0.1% SDS at 0.1×SSC and 65° C. in the washing stage. The use of much higher stringent conditions makes it possible to obtain polynucleotides having higher homology.

The present invention also relates to an expression vector or expression cassette containing the transcriptional regulatory region of perilla anthocyanin 3-acyltransferase, and to a non-human host transformed by the expression vector or expression cassette.

In the description, an "expression cassette" refers to a DNA fragment in which a promoter and terminator are ligated to an arbitrary nucleic acid.

Moreover, the present invention relates to a plant, progeny thereof, or vegetative proliferation product, part or tissue thereof, and particularly a petal or cut flower thereof, that has a useful trait such as changing color obtained by ligating the transcriptional regulatory region of perilla anthocyanin 3-acyltransferase to a useful exogenous gene. Examples of plants able to be transformed include, but are not limited to, roses, chrysanthemums, carnations, snapdragons, cyclamens, orchids, prairie gentians, freesia, gerbera, gladiolas, baby's-breath, kalanchoe, lilies, pelargonium, geraniums, petunias, torenia, tulips, rice, barley, wheat, rapeseed, potato, tomato, poplar, banana, eucalyptus, sweet potato, soybeans, alfalfa, lupines, and maize.

The present invention also relates to a processed product that uses the aforementioned cut flower (cut flower processed product). Here, a cut flower processed product includes, but is not limited to, a pressed flower, preserved flower, dry flower or resin-embedded product obtained by using the cut flower.

In the present description, the term "chrysanthemum plant" (or simply referred to as "chrysanthemum") means a plant of family Asteraceae and genus *Chrysanthemum*, and a typical example of a species thereof is *Chrysanthemum morifolium*.

EXAMPLES

The following provides a detailed explanation of the present invention through examples thereof.

Molecular biological techniques were carried out in accordance with Molecular Cloning (Sambrook and Russell, 2001) unless specifically indicated otherwise.

Example 1

Cloning of Perilla Anthocyanin 3-Acyl Transferase Chromosomal Gene

There are known to be red varieties of perilla in which anthocyanins accumulate in the leaves and green varieties in which they do not. Chromosomal DNA from the leaves of the former was prepared using a reported method (see Plant Mol. Biol., December 1997, 35(6), 915-927). This chromosomal DNA was partially decomposed with Sau3AI (Toyobo), and a fraction containing a 10 kb to 15 kb DNA fragment was recovered using a sucrose density gradient method. This fragment was then inserted into the BamHI site of EMBL3 (Promega), a type of lambda phage vector, using a known method to prepare a chromosomal DNA library. The resultant library was screened using pSAT208 (see Plant Cell Physiol., Apr. 2000, 41(4), 495-502), which is cDNA of anthocyanin 3-acyl transferase derived from perilla, as a probe. Screening of the library was in accordance with a previously reported method (see Plant Cell Physiol., July 1996, 37(5), 711-716). Plaques that hybridized with the probe were blunted and cultured, and DNA was prepared from the resultant phage.

Example 2

Nucleotide Sequence Determination of Perilla Anthocyanin 3-Acyltransferase Chromosomal Gene 10 µg of the DNA obtained above were digested with XbaI and isolated with 0.7% agarose gel followed by blotting onto Hybond-N (Amersham). When this film was hybridized in the same manner as previously described, a roughly 6.8 kb DNA fragment was found to hybridize with the probe. After digesting 20 µg of the same DNA with XbaI and isolating with 0.7% agarose gel, a roughly 6.8 kb DNA fragment was purified using GeneClean and coupled with pBluescript SKII— digested with XbaI. The resultant plasmid was designated pSPB513. The DNA sequence derived from perilla contained in this plasmid was determined by primer walking. The nucleotide sequence thereof is shown in SEQ ID NO. 4. This sequence is a region that demonstrates high homology with anthocyanin 3-acyl transferase cDNA in the form of pSAT208, the amino acid sequence (SEQ ID NO. 6) of protein encoded by this region was observed to demonstrate substitutions of 19 amino acid residues and deletion of 2 amino acid residues in comparison with the amino acid sequence encoded by pSAT208, and there were no introns observed. In addition, the sequence of the region demonstrating high homology with pSAT208 contained a 3438 bp sequence upstream from ATG that was thought to be the initiation codon, and a 2052 bp sequence downstream from TAA that was thought to be the stop codon thereof. A different open reading frame (ORF, SEQ ID NO. 5), which was not anthocyanin 3-acyl transferase, was present in the aforementioned 3438 bp sequence. The following experiment was conducted to amplify the transcriptional regulatory region of perilla anthocyanin 3-acyl transferase gene, excluding this portion.

Example 3

Amplification of Transcriptional Regulatory Region of Perilla Anthocyanin 3-Acyl Transferase Gene PCR (holding for 1 minute at 95° C. followed by 25 cycles of a reaction consisting of 1 minute at 52° C., 2 minutes at 72° C. and 1 minute at 95° C.) was carried out using 1 ng of pSPB513 as template and two types of primers (5'-AAGCTTAACTATTATGATCCCACAGAG-3' (SEQ ID NO. 7, underline indicates HindIII recognition sequence) and 5'-GGATCCGGCGGTGTTGAACGTAGC-3' (SEQ ID NO. 8, underline indicates BamHI recognition sequence)). The amplified roughly 1.1 kb DNA fragment was digested with HindIII and BamHI.

The plasmid pSPB567 described in Patent Document 4 (in which pansy-derived flavonoid 3',5'-hydroxylase gene is coupled to the 3'-side of cauliflower mosaic 35S promoter to which has been added an enhancer, and in which a nopaline synthase terminator is further coupled to the 3'-side thereof) was digested with PacI, and a DNA fragment containing pansy-derived F3'5'H gene was cloned into the PacI site of pBin+ (see Transgenic Research, 4, 288-290, 1995). A plasmid in which the cauliflower mosaic 35S promoter to which enhancer was added is present close to the AscI site of pBin+ in the resultant plasmid was designated pSPB575. This plasmid was then digested with HindIII and BamHI, and a DNA fragment obtained by digesting a roughly 1.1 kb DNA fragment containing the transcriptional regulatory region of the aforementioned perilla anthocyanin 3-acyl transferase with HindIII and BamHI was inserted therein. The resultant plasmid was designated pSFL205 (see FIG. 1).

Figure 2:
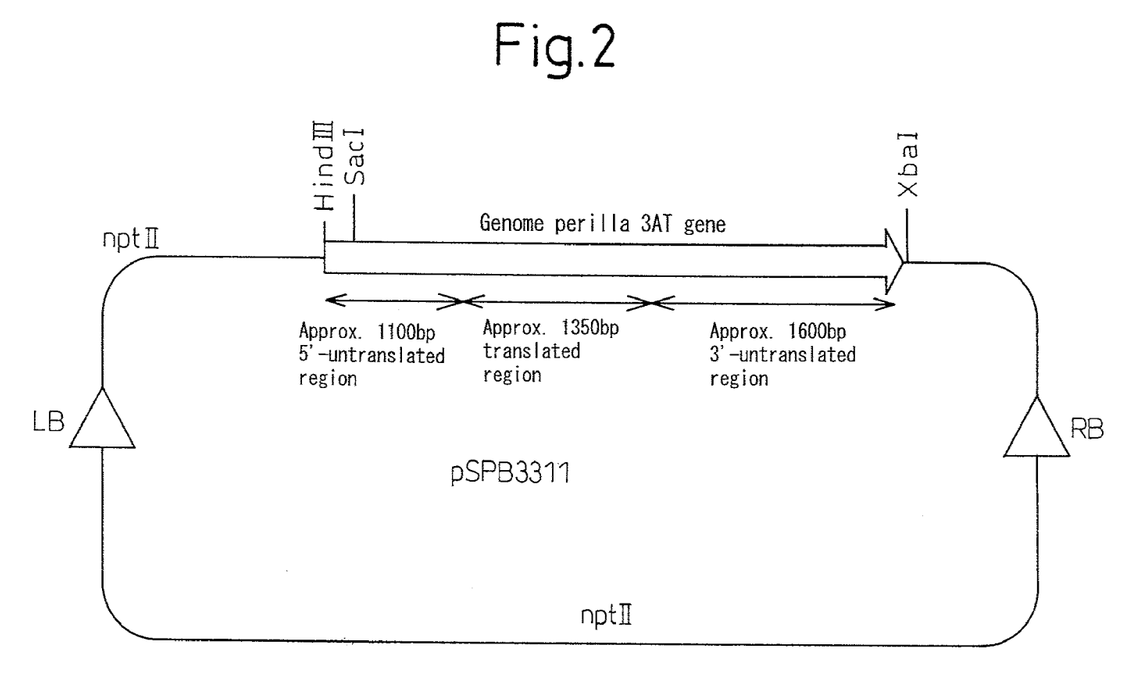
FIG. 2 is a schematic diagram of a binary vector pSPB3311 used to transform perilla 3AT gene.

Plasmid pSFL205 was digested with HindIII and SacI, and a roughly 100 bp DNA fragment was recovered. This DNA fragment, a roughly 4 kb DNA fragment obtained by digesting pSPB513 with SacI and XbaI, and a plasmid pBin+ digested with HindIII and XbaI were coupled to obtain plasmid pSPB3311 (see FIG. 2). This plasmid pSPB3311 is a binary vector that contains the nucleotide sequence indicated in SEQ ID NO. 2, and contains the transcriptional regulatory region of perilla anthocyanin 3-acyl transferase gene and an untranslated region of the 3'-side thereof.

Example 4

Expression of Perilla Anthocyanin 3-Acyltranferase Chromosome Gene in Petunia The plasmid pSPB3311 (binary vector) obtained in Example 3 was transformed in petunia variety Baccara Red (Sakata Seed) according to the *Agrobacterium* method using a leaf disc to obtain about 20 lines of transgenic plants. Transformation was in accordance with a known method (Plant J. 1994, 5, p. 81). In addition, petunia variety Baccara Red (Sakata Seed) was similarly transformed with pBELA11 described in Patent Document 1 (binary vector for expressing lavender anthocyanin 3-acyltransferase gene in plants in which lavender anthocyanin 3-acyltransferase cDNA is inserted between repeatedly enhanced cauliflower mosaic virus 35S promoter and nopaline synthase-derived terminator) to obtain about 20 lines of transgenic plants.

The flower color of the petunias transformed using *Agrobacterium* containing the above two types of binary vectors (pSPB3311 or pBELA11) exhibited a relatively light red color in comparison with the Baccara Red prior to transformation. Each of the representative recombinant petunias were designated PT266-7 and PT267-1. The anthocyanins of the petals of these petunias were analyzed using the method described in Patent Document 4. In the flower petals of the recombinant petunias, the amount of anthocyanin having a longer high-performance liquid chromatography retention time than the host increased, and their absorption spectra were observed to have slopes in the vicinity of 310 nm. This indicates that the amount of anthocyanin to which aromatic acyl groups are bonded increased in the recombinant petunias, and that the anthocyanin 3-acyltransferase gene of the transformed perilla or lavender functioned in petunia.

Moreover, anthocyanins of the host and transformed petunia were analyzed by LC-FT-ICR-MS (J. Japan Soc. Hort. Sci., 77, 94-102 (2008) and Plant J., 54, 949-962). The use of this technique makes it possible to precisely measure the mass spectrum of the anthocyanins and obtain MS/MS spectra by tandem mass spectrometry. Anthocyanins demonstrating molecular weights and MS/MS spectra coinciding with cyanidin (coumaroyl) glucoside (m/z 595.143717, MS/MS 287), delphinidin (coumaroyl) glucoside (m/z 611.139648, MS/MS 303.1) and peonidin (coumaroyl) glucoside (m/z 609.161119, MS/MS 303.1) not observed in the host were detected (m/z and m/z of MS/MS are shown in parentheses).

The amounts of the transcripts of the enzyme genes involved in anthocyanin synthesis are known to change depending on the growth stage of petunia petals. For example, if the growth stages of petunia petals are divided into five stages and the expression amount of flavonoid 3',5'-hydroxylase gene in the petals is investigated at each stage, the gene is strongly expressed from the stage at which the petunia petals begin to bloom until the stage soon after, while the expressed amount decreases in mature petals (see PCT/AU92/00334). On the other hand, genes controlled by a constitutive promoter demonstrated a constant expression level regardless of the petal growth stage.

When petunia petals transformed with pSPB3311 were similarly divided into five stages and examined for expression of perilla anthocyanin 3-acyltranferase gene, the gene was strongly expressed from the stage at which the petals begin to bloom until the stage soon after blooming, while the expression level decreased in mature petals. On the other hand, petunias transformed with pBELA11 demonstrated a constant amount of the transcription product regardless of the growth stage. These results indicate that the transcriptional regulatory region of perilla-derived anthocyanin 3-acyltransferase is able to transcribe structural genes in petunia that is a different species from perilla, and that this transcription occurs in parallel with genes of anthocyanin biosynthases, thereby clearly demonstrating that such transcriptional regulatory regions are useful for altering flower color. In other words, in the present embodiment, the promoter region and terminator region of the chromosome gene of anthocyanin 3-acyltransferase derived from perilla were indicated to alter the structure of anthocyanins in flower petals or organs in which anthocyanins accumulate, namely function at a level required to alter flower color, and this means that these regions are useful for artificially expressing genes of different species.

Example 5

Figure 1:
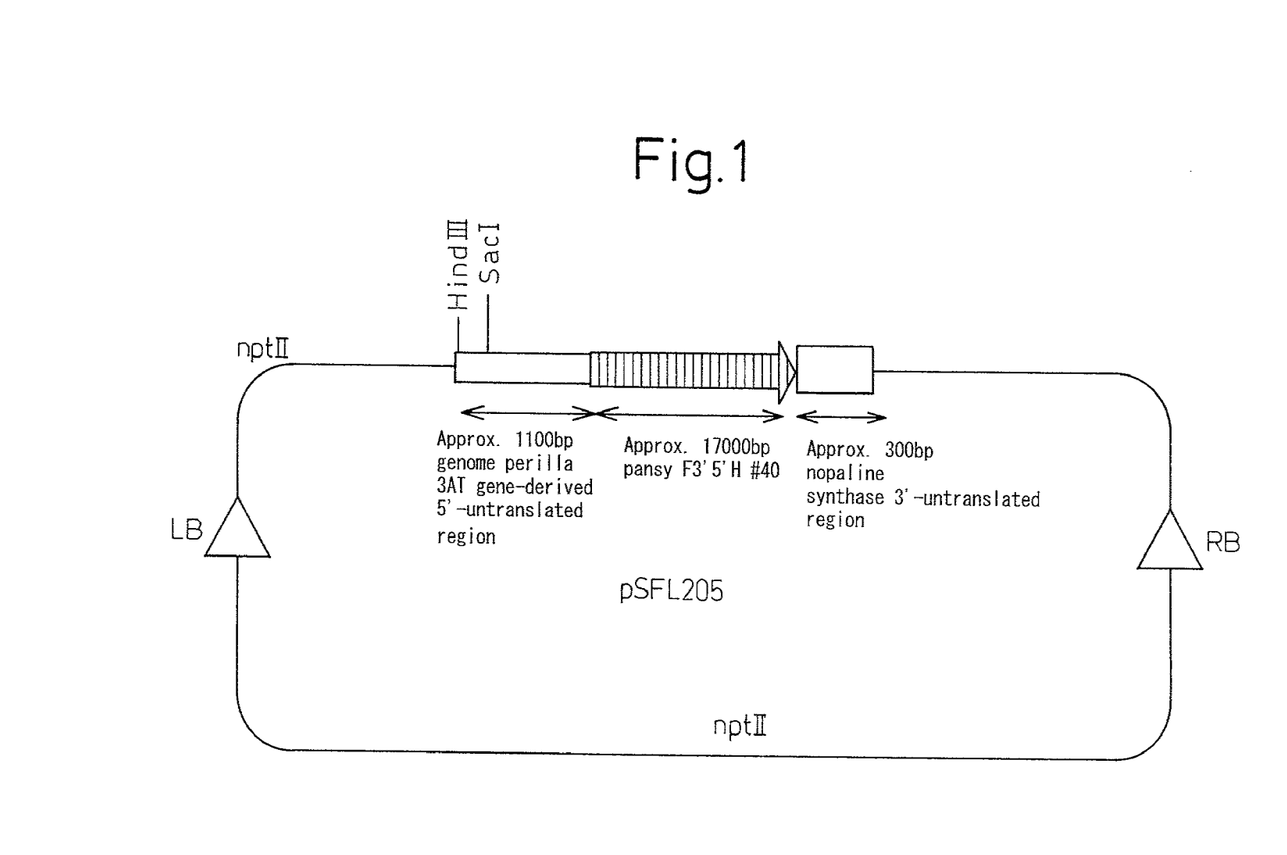
FIG. 1 is a schematic diagram of pSLF205.

Expression of Perilla Anthocyanin 3-Acyltranferase Transcriptional Regulatory Region in Rose pSFL205 indicated in FIG. 1 was transformed into rose cultivar Lavande to acquire 27 line of transgenic rose plant bodies. Numerous methods regarding rose transformation have previously been reported (see, for example, Firoozababy, et al., Bio/Technology 12:883-888 (1994), U.S. Pat. No. 5,480,789, U.S. Pat. No. 5,792,927, EP 536327A1, and U.S. Patent Application Publication No. 2001-0007157A1), and transformation can be carried out in accordance with these methods.

More specifically, rose calli derived from the leaves of sterile seedlings were immersed for 5 minutes in a culture of *Agrobacterium tumefaciens* strain AglO (Lazo, et al., Bio/Technology 9:963-967 (1991), and after wiping off any excess culture liquid with sterile filter paper, the calli were transferred to sub-culturing medium and co-cultured for 2 days in a dark location.

Subsequently, the calli were washed with MS liquid medium containing 400 mg/l of carbenicillin, and transferred to selective/sterilization medium in which 50 mg/l of kanamycin and 200 mg/l of carbenicillin were added to the sub-culturing medium. Kanamycin-resistant calli were selected by repeatedly transplanting and culturing those portions that grew normally without showing growth inhibition on the selective medium.

The transformed calli that demonstrated kanamycin resistance were cultured in regeneration medium containing 50 mg/l of kanamycin and 200 mg/l of carbenicillin to obtain kanamycin-resistant chutes. The resultant shoots were allowed to root in 1/2 MS medium followed by acclimation. The acclimated individuals were then potted and allowed to bloom by cultivating in a contained greenhouse.

The amount of anthocyanidin contained in the rose petals was measured in the manner described below. 0.5 g of freeze-dried petals were extracted with ultrasonication for 20 minutes in 4 ml of 50% acetonitrile ($CH_3CN$) containing 0.1% TFA followed by filtering with a 0.45 µm filter. 0.2 ml of the filtrate were dried to a solid under reduced pressure in a glass test tube followed by dissolving in 0.2 ml of 6 N hydrochloric acid (HCl) and hydrolyzing for 20 minutes at 100° C. The decomposed anthocyanidin was extracted with 0.2 ml of 1-pentanol and the organic layer was analyzed by HPLC under the following conditions. An ODS-A312 column (6 mmϕ×15 cm, YMC), a 15:20:65 solution of AcOH:MeOH:$H_2O$ was used for the mobile phase, and extraction was carried out at a flow rate of 1 ml/min. Detection was carried out by measuring the spectrum at 600 nm to 400 nm with an SPD-M10A photodiode array detector (Shimadzu), identifying the absorbance maximum (λmax) and retention time (R.T.), and quantifying based on the area of absorbance at 520 nm. The R.T and λmax of delphinidin and cyanidin under these HPLC conditions were 4.0 minutes and 5.2 minutes and 534 nm and 525 nm, respectively. Identification and quantification were carried out using delphinidin hydrochloride and cyanidin hydrochloride purchased from Funakoshi as standards.

The content of delphinidin contained in the recombinant petals (percentage of delphinidin out of the total amount of anthocyanidins) demonstrated a maximum of 51% and average of 20.5%. These results indicate that the transcriptional regulatory region of perilla anthocyanin 3-acyltransferase is able to transcribe a target gene in plants of different species from perilla.

INDUSTRIAL APPLICABILITY

A promoter region thought to regulate transcription of enzyme genes in the leaves of perilla, namely a transcriptional regulatory region of perilla anthocyanin 3-acyltranferase, was determined to be able to function as a transcriptional regulatory region in flower petals of different species in the form of petunias and roses. Thus, transcription of exogenous genes can be specifically induced in tissues such as flowers in which anthocyanins accumulate by using this transcriptional regulatory region of perilla anthocyanin 3-acyltransferase. Although examples of transcribed exogenous genes include genes associated with flower color and fragrance, they are not limited thereto.

The invention claimed is:

1. An expression vector or expression cassette containing a nucleic acid containing the nucleotide sequence indicated in SEQ ID NO. 1.

2. The expression vector or expression cassette according to claim 1, containing the nucleotide sequence indicated in SEQ ID NO: 2.

3. A plant other than chrysanthemum, progeny thereof, or vegetative proliferation product, part or tissue thereof, transformed with the expression vector or expression cassette according to claim 1.

4. The plant other than chrysanthemum, progeny thereof, or vegetatively propagated product, part or tissue thereof according to claim 3, which is a cut flower.

5. A cut flower processed product obtained from the cut flower according to claim 4.

* * * * *